United States Patent
Suzuki et al.

(10) Patent No.: US 9,844,685 B2
(45) Date of Patent: *Dec. 19, 2017

(54) RADIOTHERAPY EQUIPMENT CONTROL DEVICE, RADIOTHERAPY EQUIPMENT CONTROL METHOD, AND PROGRAM EXECUTED BY COMPUTER FOR RADIOTHERAPY EQUIPMENT

(71) Applicants: HITACHI, LTD., Tokyo (JP); KYOTO UNIVERSITY, Kyoto (JP)

(72) Inventors: Yasunobu Suzuki, Tokyo (JP); Mitsuhiro Nakamura, Kyoto (JP); Akira Sawada, Kyoto (JP); Masahiro Yamada, Kyoto (JP)

(73) Assignees: HITACHI, LTD., Tokyo (JP); KYOTO UNIVERSITY, Kyoto (JP)

( * ) Notice: Subject to any disclaimer, the term of this patent is extended or adjusted under 35 U.S.C. 154(b) by 526 days.

This patent is subject to a terminal disclaimer.

(21) Appl. No.: 14/380,825

(22) PCT Filed: Feb. 27, 2013

(86) PCT No.: PCT/JP2013/055063
§ 371 (c)(1),
(2) Date: Aug. 25, 2014

(87) PCT Pub. No.: WO2013/129442
PCT Pub. Date: Sep. 6, 2013

(65) Prior Publication Data
US 2015/0038763 A1    Feb. 5, 2015

(30) Foreign Application Priority Data
Feb. 28, 2012    (JP) .................. 2012-042173

(51) Int. Cl.
*A61N 5/00*    (2006.01)
*A61N 5/10*    (2006.01)
*A61B 90/00*    (2016.01)

(52) U.S. Cl.
CPC ............ *A61N 5/1049* (2013.01); *A61B 90/39* (2016.02); *A61N 5/1067* (2013.01);
(Continued)

(58) Field of Classification Search
CPC ........ A61N 5/00; A61N 5/103; A61N 5/1048; A61N 5/1049; A61N 5/1051; A61N 5/1064
(Continued)

(56) References Cited

U.S. PATENT DOCUMENTS 6,307,914 B1    10/2001    Kunieda et al.
6,501,981 B1    12/2002    Schweikard et al.
(Continued)

FOREIGN PATENT DOCUMENTS

CN    101032650    9/2007
EP    1 832 313    9/2007
(Continued)

OTHER PUBLICATIONS

Notice of Allowance dated Sep. 1, 2015 in corresponding Japanese Application No. 2012-042173, with English translation.
(Continued)

*Primary Examiner* — John Lacyk

(57) ABSTRACT

A radiotherapy equipment control device acquires reference position information for a specific location at a reference time. Furthermore, representative point reference position information is generated from reference position information for a plurality of markers at the reference time, and relative position information up to the reference position information for the specific location is generated. Moreover, representative point position information at another time is generated from the position information for a plurality of markers in a subject at the other time, which differs from the reference time. In addition, position information for the specific location at the other time is generated from the representative point position information and the relative position information. In this case, representative point reference position information and representative position information are generated on the basis of the position information and reference position information for the plurality of markers, said information having been weighted by weighting factors.

7 Claims, 6 Drawing Sheets

(52) U.S. Cl.
CPC .... *A61N 5/1082* (2013.01); *A61N 2005/1051* (2013.01); *A61N 2005/1061* (2013.01); *A61N 2005/1074* (2013.01)

(58) Field of Classification Search
USPC .......................................................... 600/1–8
See application file for complete search history.

(56) References Cited

U.S. PATENT DOCUMENTS

| | | | |
|---|---|---|---|
| 9,393,444 B2* | 7/2016 | Suzuki | A61N 5/1037 |
| 2006/0074292 A1* | 4/2006 | Thomson | A61B 6/037 |
| | | | 600/411 |
| 2006/0241387 A1 | 10/2006 | Nagamine et al. | |
| 2007/0291895 A1 | 12/2007 | Yin et al. | |
| 2011/0163243 A1 | 7/2011 | Iwata | |

FOREIGN PATENT DOCUMENTS

| | | |
|---|---|---|
| JP | 2006-247268 | 9/2006 |
| JP | 2007-505690 | 3/2007 |
| JP | 2007-236760 | 9/2007 |
| JP | 2008-80131 | 4/2008 |
| JP | 2009-178323 | 8/2009 |
| JP | 2010-284513 | 12/2010 |
| JP | 2011-200542 | 10/2011 |
| WO | 2010/143267 | 12/2010 |
| WO | 2011/059061 | 5/2011 |

OTHER PUBLICATIONS

Extended European Search Report dated Oct. 1, 2015 in corresponding European Application No. 13754204.9.

International Search Report dated Apr. 16, 2013 in corresponding International Application No. PCT/JP2013/055063.

Translation of Written Opinion of the International Searching Authority dated Apr. 16, 2013 in corresponding International Application No. PCT/JP2013/055063.

First Office Action dated Dec. 2, 2015 in Chinese Application No. 201380004772.6 (with English translation).

* cited by examiner

| | DISPLACEMENT AMOUNT (x) OF SPECIFIC PORTION | DISPLACEMENT AMOUNT (y) OF MARKER |
|---|---|---|
| $A_{t1}$ | $x_1$ | $y_1$ |
| $A_{t2}$ | $x_2$ | $y_2$ |
| $A_{t3}$ | $x_3$ | $y_3$ |

US 9,844,685 B2

1
RADIOTHERAPY EQUIPMENT CONTROL DEVICE, RADIOTHERAPY EQUIPMENT CONTROL METHOD, AND PROGRAM EXECUTED BY COMPUTER FOR RADIOTHERAPY EQUIPMENT

TECHNICAL FIELD

The present invention relates to a radiotherapy equipment control device which controls radiotherapy equipment by specifying a position of a specific portion within a subject using a plurality of markers.

Priority is claimed on Japanese Patent Application No. 2012-042173, filed on Feb. 28, 2012, the content of which is incorporated herein by reference.

BACKGROUND ART

Radiotherapy equipment for treating a patient by irradiating his or her affected part with therapeutic radiation is known.

In radiotherapy, it is desirable that radiation treatment using therapeutic radiation on an affected part be accurately performed to reduce a dose radiated to normal cells around the affected part and reduce any influence on the normal cells.

Here, because a position of the affected part (specific portion) varies with the passage of time due to a subject's respiration or the like, it is also necessary to vary an irradiation position of radiation therewith and perform tracking irradiation. Thus, technology for embedding a marker inside the subject, pre-measuring relative positions of the marker and the affected part using a computed tomography (CT) image or the like, and estimating a position of the affected part from relative positions to positions of a plurality of markers after a predetermined time has been proposed (for example, see Patent Literature 1).

PRIOR ART LITERATURE

Patent Literature

[Patent Literature 1]
Japanese Unexamined Patent Application, First Publication No. 2007-236760

DISCLOSURE OF INVENTION

Problems to be Solved by the Invention

However, in the radiotherapy equipment of Patent Literature 1, it is difficult to accurately detect a position of the specific portion because displacement amounts or displacement directions of the specific portion and the marker are likely to be different when a marker is located at a position within the body of the subject away from the specific portion.

The present invention has been made to solve the above-described problem, and an objective of the invention is to provide a radiotherapy equipment control device, a radiotherapy equipment control method, and a program executed by a computer of radiotherapy equipment that enable a position of an irradiation target to be accurately estimated using a plurality of markers.

Means for Solving the Problems

In order to solve the above-described problems, the present invention proposes the following means.

A radiotherapy equipment control device is provided for specifying a position of a specific portion from positions of a plurality of markers located in the vicinity of the specific portion within a subject and controlling radiotherapy equipment, the radiotherapy equipment control device including: a reference position information acquisition unit configured to acquire reference position information representing a position within the body of the subject at a reference time of each of the specific portion and the plurality of markers; a representative point reference position information computation unit configured to generate reference position information representing a position within the body of the subject at the reference time of a representative point of the plurality of markers from the reference position information of the plurality of markers; a relative position information computation unit configured to generate relative position information using a position represented by the reference position information of the representative point as a base point for a position represented by the reference position information of the specific portion; a marker position information acquisition unit configured to acquire position information of the plurality of markers within the body of the subject at another time different from the reference time; a representative point position information computation unit configured to generate position information of the representative point within the body of the subject at the other time of the plurality of markers from the position information of the plurality of markers; and a specific portion position information computation unit configured to generate position information of the specific portion at the other time from the position information of the representative point and the relative position information, wherein the representative point reference position information computation unit specifies a weight coefficient for each of the plurality of markers and generates the reference position information of the representative point based on the position information of the plurality of markers weighted by the weight coefficient, and wherein the representative point position information computation unit generates the position information of the representative point based on the position information of the plurality of markers weighted by the weight coefficient.

According to this radiotherapy equipment control device, it is possible to compute the position information of the representative point and detect the position of the specific portion based on the position information of the plurality of markers weighted by the weight coefficient.

In the radiotherapy equipment control device, the representative point reference position information computation unit and the representative point position information computation unit compute a reciprocal of a distance between the specific portion and the marker for each of the plurality of markers and specify the computed reciprocal as the weight coefficient for each of the plurality of markers.

According to this configuration, it is possible to decrease the weight coefficient of the marker located at a position away from the specific portion, and, in contrast, it is possible to increase the weight coefficient of the marker located at a position close to the specific portion. Thus, it is possible to obtain the position information of the representative point and detect the position information of the specific portion by increasing a weight of the marker which is close to the specific portion and has a displacement amount or a displacement direction similar to the specific portion rather than the marker which is away from the specific portion and has a different displacement amount or displacement direction from the specific portion.

In the radiotherapy equipment control device, the representative point reference position information computation unit and the representative point position information computation unit compute and specify the weight coefficient as a correlation coefficient between displacement amounts from a reference position for the specific portion and displacement amounts from a reference position for the marker at a plurality of different times.

According to this configuration, the weight coefficient may decrease if a correlation between the displacement amounts of the specific portion and the marker is low, and, in contrast, the weight coefficient may increase if the correlation between the displacement amounts of the specific portion and the marker is high. Thus, it is possible to obtain the position information of the representative point and estimate the position information of the specific portion by increasing a weight of the marker having a high correlation of the displacement amount with the specific portion rather than the marker having a low correlation of the displacement amount with the specific portion.

In the radiotherapy equipment control device, the representative point reference position information computation unit and the representative point position information computation unit specify the weight coefficient by an arbitrary input through an input means based on a correlation between displacements of the specific portion and the marker or a distance between the specific portion and the marker.

According to this configuration, the operator can arbitrarily determine and input the weight coefficient, obtain the position information of the representative point, and detect the position information of the specific portion based on the displacement correlation or the distance between the specific portion and the marker.

In the radiotherapy equipment control device, the representative point reference position information computation unit and the representative point position information computation unit specify the weight coefficient of at least one marker among the plurality of markers as 0.

According to this configuration, it is possible to exclude the marker having a different displacement amount or displacement direction from the specific portion from computation of the position information of the representative point. Thus, it is possible to designate the marker to be used in computation of the position information of the representative point.

In addition, a radiotherapy equipment control method is provided for controlling radiotherapy equipment in specifying a position of the specific portion from positions of a plurality of markers located in the vicinity of the specific portion of a subject, the radiotherapy equipment control method including: acquiring reference position information representing a position within the body of the subject at a reference time of each of the specific portion and the plurality of markers; generating reference position information representing a position within the body of the subject at the reference time of a representative point of the plurality of markers from the reference position information of the plurality of markers; generating relative position information using a position represented by the reference position information of the representative point as a base point for a position represented by the reference position information of the specific portion; acquiring position information of the plurality of markers within the body of the subject at another time different from the reference time; generating position information of the representative point within the body of the subject at the other time of the plurality of markers from the position information of the plurality of markers; and generating position information of the specific portion at the other time from the position information of the representative point and the relative position information, wherein the reference position information of the representative point is generated based on the position information of the plurality of markers weighted by the weight coefficient specified for each of the plurality of markers, and wherein the position information of the representative point is generated based on the position information of the plurality of markers weighted by the weight coefficient.

According to this configuration, it is possible to compute the position information of the representative point and estimate the position of the specific portion based on the position information of the plurality of markers weighted by the weight coefficient.

In addition, a program is provided for causing a computer of a radiotherapy equipment control device for controlling radiotherapy equipment in specifying a position of a specific portion from positions of a plurality of markers located in the vicinity of the specific portion within a subject that comprises: a reference position information acquisition means configured to acquire reference position information representing a position within the body of the subject at a reference time of each of the specific portion and the plurality of markers; a representative point reference position information computation means configured to generate reference position information representing a position within the body of the subject at the reference time of a representative point of the plurality of markers from the reference position information of the plurality of markers; a relative position information computation means configured to generate relative position information of a position represented by the reference position information of the specific portion using a position represented by the reference position information of the representative point as a base point a marker position information acquisition means configured to acquire position information of the plurality of markers within the body of the subject at another time different from the reference time; a representative point position information computation means configured to generate position information of the representative point within the body of the subject at the other time of the plurality of markers from the position information of the plurality of markers; and a specific portion position information computation means configured to generate position information of the specific portion at the other time from the position information of the representative point and the relative position information, wherein the representative point reference position information computation means specifies a weight coefficient for each of the plurality of markers and generates the reference position information of the representative point based on the position information of the plurality of markers weighted by the weight coefficient, and wherein the representative point position information computation means generates the position information of the representative point based on the position information of the plurality of markers weighted by the weight coefficient.

According to this configuration, it is possible to compute the position information of the representative point and detect the position of the specific portion based on the position information of the plurality of markers weighted by the weight coefficient.

Effects of the Invention

According to a radiotherapy equipment control device in an aspect of the present invention, it is possible to detect a position of a specific portion more accurately than in the past even when the specific portion is displaced by weighting each of a plurality of markers-using a weight coefficient according to a distance from the specific portion. Thereby, it is possible to accurately irradiate the specific portion with radiation in radiotherapy.

PREFERRED EMBODIMENTS FOR CARRYING OUT THE INVENTION

Hereinafter, an embodiment according to the present invention will be described with reference to the drawings.

Figure 1:
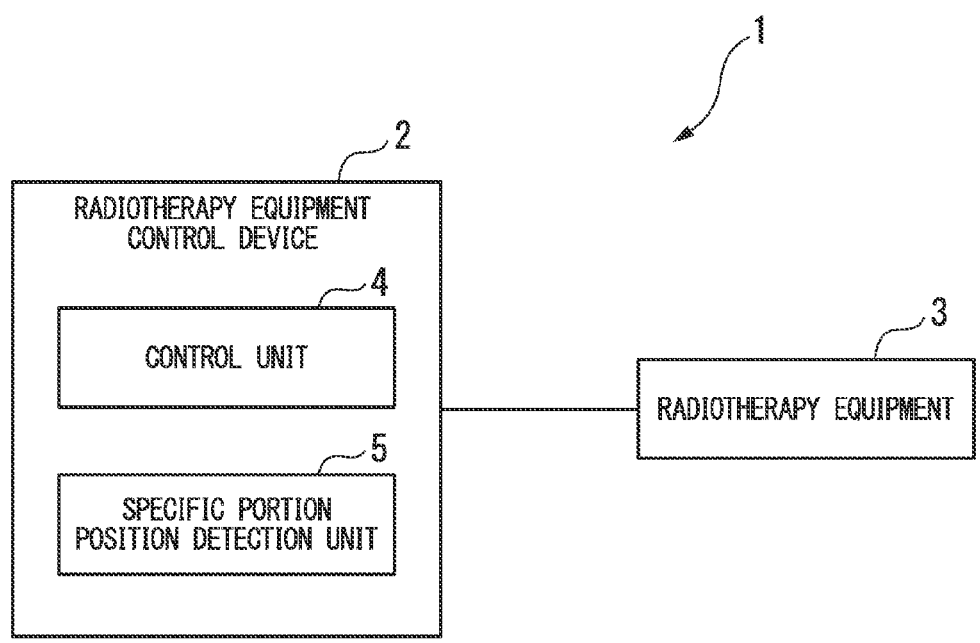
FIG. 1 is a block diagram of a radiotherapy system having a radiotherapy equipment control device of the present invention.

A radiotherapy equipment control device 2 of this embodiment is applied to a radiotherapy system 1 as illustrated in FIG. 1. The radiotherapy system 1 includes radiotherapy equipment 3 and a radiotherapy equipment control device 2. The radiotherapy equipment 3 and the radiotherapy equipment control device 2 are connected so that information can be transmitted bi-directionally. The radiotherapy equipment control device 2 is a computer such as a personal computer. The radiotherapy equipment control device 2 includes a control unit 4 and a specific portion position detection unit 5. The control unit 4 controls the radiotherapy equipment 3 based on position information of a specific portion 61 detected in the specific portion position detection unit 5.

Figure 2:
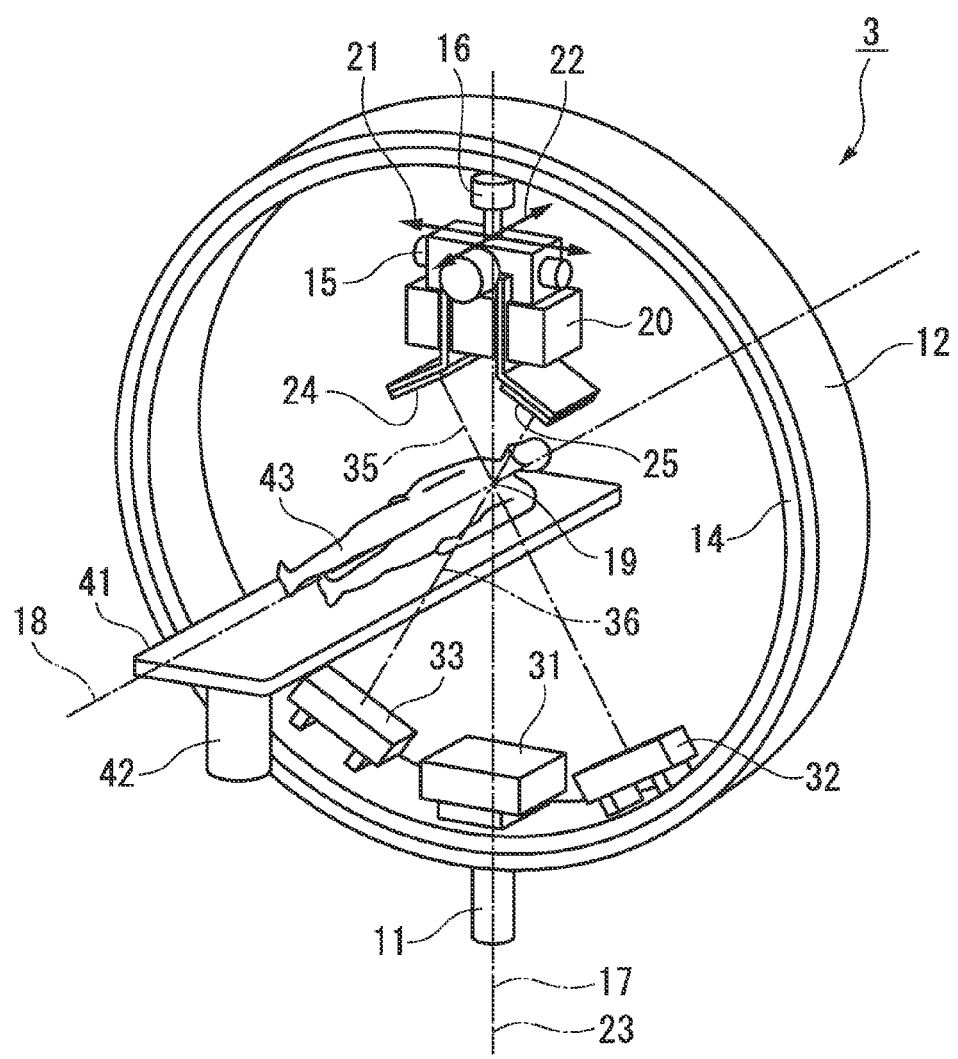
FIG. 2 is a perspective view illustrating radiotherapy equipment.

FIG. 2 illustrates the radiotherapy equipment 3. The radiotherapy equipment 3 is provided with a turning drive device 11, an O ring 12, a traveling gantry 14, a swing mechanism 15, and a therapeutic radiation irradiation device 16. The turning drive device 11 supports the O ring 12 on a base so that the O ring 12 is rotatable around a rotation axis 17, and is controlled by the radiotherapy equipment control device 2 to rotate the O ring 12 around the rotation axis 17. The rotation axis 17 is parallel with a vertical direction. The O ring 12 is formed in a ring shape centered on a rotation axis 18, and supports the traveling gantry 14 so that the traveling gantry 14 is rotatable around the rotation axis 18.

The rotation axis 18 is perpendicular to the vertical direction, and passes through isocenter 19 included in the rotation axis 17.

The rotation axis 18 is further fixed with respect to the O ring 12, that is, rotates around the rotation axis 17 along with the O ring 12. The traveling gantry 14 is formed in a ring shape centered on the rotation axis 18, and arranged to be concentric with the ring of the O ring 12. The radiotherapy equipment 3 is further provided with a traveling drive device (not illustrated). The traveling drive device is controlled by the radiotherapy equipment control device 2 to rotate the traveling gantry 14 around the rotation axis 18.

The swing mechanism 15 is fixed inside the ring of the traveling gantry 14 to support the therapeutic radiation irradiation device 16 to the traveling gantry 14 so that the therapeutic radiation irradiation device 16 is arranged inside the traveling gantry 14. The swing mechanism 15 has a pan axis 21 and a tilt axis 22. The tilt axis 22 is fixed with respect to the traveling gantry 14 and is parallel to the rotation axis 18 without intersecting the rotation axis 18. The pan axis 21 is orthogonal to the tilt axis 22. The swing mechanism 15 is controlled by the radiotherapy equipment control device 2 to rotate the therapeutic radiation irradiation device 16 around the pan axis 21 and rotate the therapeutic radiation irradiation device 16 around the tilt axis 22.

The therapeutic radiation irradiation device 16 is controlled by the radiotherapy equipment control device 2 to radiate therapeutic radiation 23. The therapeutic radiation 23 is radiated approximately along a straight line passing through an intersection at which the pan axis 21 and the tilt axis 22 intersect. The therapeutic radiation 23 is formed to have a uniform strength distribution. The therapeutic radiation irradiation device 16 includes a multi-leaf collimator (MLC) 20. The MLC 20 is controlled by the radiotherapy equipment control device 2, and changes a shape of an irradiation field by shielding part of the therapeutic radiation 23 when the therapeutic radiation 23 is radiated to the patient.

As the therapeutic radiation irradiation device 16 is supported on the traveling gantry 14 in this manner, the therapeutic radiation 23 approximately constantly passes through the isocenter 19 even when the O ring 12 is rotated by the turning drive device 11 or the traveling gantry 14 is rotated by the traveling drive device once adjustment is performed by the swing mechanism 15 so that the therapeutic radiation irradiation device 16 is directed toward the isocenter 19. That is, the radiation of the therapeutic radiation 23 can be radiated from an arbitrary direction to the isocenter 19 by performing the traveling and/or turning.

The radiotherapy equipment 3 is further provided with a plurality of imager systems. That is, the radiotherapy equipment 3 is provided with diagnostic X-ray sources 24 and 25 and sensor arrays 32 and 33.

The diagnostic X-ray source 24 is supported on the traveling gantry 14. The diagnostic X-ray source 24 is arranged inside the ring of the traveling gantry 14 and arranged at a position at which an angle formed by a line segment connecting the isocenter 19 and the diagnostic X-ray source 24 and a line segment connecting the isocenter 19 and the therapeutic radiation irradiation device 16 is an acute angle. The diagnostic X-ray source 24 is controlled by the radiotherapy equipment control device 2 to radiate diagnostic X-rays 35 toward the isocenter 19. The diagnostic X-rays 35 are radiated from one point included in the diagnostic X-ray source 24, and are cone beams with conical shape, which vertex is the one point. The diagnostic X-ray source 25 is supported on the traveling gantry 14. The diagnostic X-ray source 25 is arranged inside the ring of the traveling gantry 14 and arranged at a position at which an angle formed by a line segment connecting the isocenter 19 and the diagnostic X-ray source 25 and a line segment connecting the isocenter 19 and the therapeutic radiation irradiation device 16 is an acute angle. The diagnostic X-ray source 25 is controlled by the radiotherapy equipment control device 2 to radiate diagnostic X-rays 36 toward the isocenter 19. The diagnostic X-rays 36 are radiated from one point included in the diagnostic X-ray source 25, and are cone beams with conical shape, which vertex is the one point.

The sensor array 32 is supported on the traveling gantry 14. The sensor array 32 receives the diagnostic X-rays 35 radiated by the diagnostic X-ray source 24 and transmitted through a subject around the isocenter 19 to generate a transmission image of the subject. The sensor array 33 is supported on the traveling gantry 14. The sensor array 33 receives the diagnostic X-rays 36 radiated by the diagnostic X-ray source 25 and transmitted through the subject around the isocenter 19 to generate a transmission image of the subject. Flat panel detectors (FPDs) and X-ray image intensifiers (IIs) are shown as examples of the sensor arrays 32 and 33.

The radiotherapy equipment 3 is further provided with a sensor array 31. The sensor array 31 is arranged so that a line segment connecting the sensor array 31 and the therapeutic radiation irradiation device 16 passes through the isocenter 19, and is fixed inside the ring of the traveling gantry 14. The sensor array 31 receives light of the therapeutic radiation 23 radiated by the therapeutic radiation irradiation device 16 and transmitted through the subject around the isocenter 19 to generate a transmission image of the subject. FPD and X-ray II are shown as examples of the sensor array 31.

The radiotherapy equipment 3 is further provided with a couch 41 and a couch drive device 42. The couch 41 is used for a patient 43 to be treated by the radiotherapy system 1 to lie on. The couch 41 is provided with a fixing tool (not illustrated). This fixing tool fixes the patient to the couch 41 so that the patient does not move. The couch drive device 42 supports the couch 41 on the base and moves the couch 41 being controlled by the radiotherapy equipment control device 2.

Figure 3:
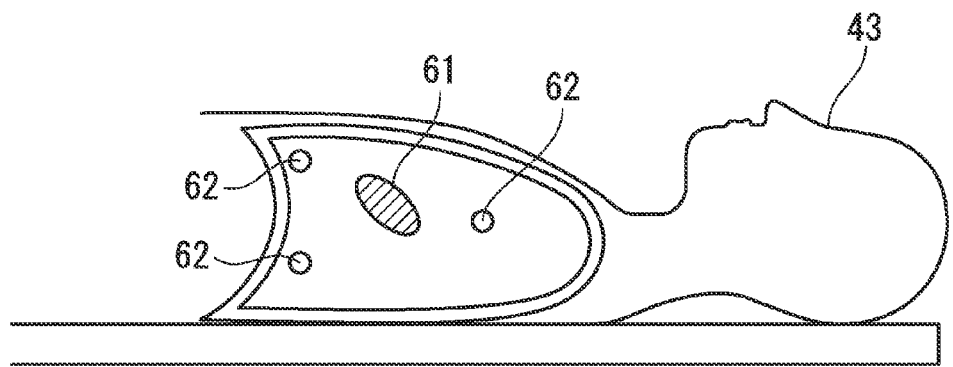
FIG. 3 is a cross-sectional view illustrating a specific portion and markers within a patient (subject).

FIG. 3 illustrates a patient (subject) 43. The patient 43 has a specific portion 61 inside the body. The specific portion 61 represents an affected part of the patient 43, and is a portion to be irradiated with the therapeutic radiation 23. As an example of specific portion 61, part of a lung is illustrated. In addition, a plurality of markers 62 are arranged within the body of the patient 43.

The marker 62 is a small piece of metal, such as gold, embedded in the vicinity of the specific portion 61 intended to be stayed at a predetermined position for the specific portion 61 for detecting a position of the specific portion 61. The marker 62 may be embedded by injection into the subject from a needle of a syringe or may be embedded according to another method such as surgery.

Figure 4:
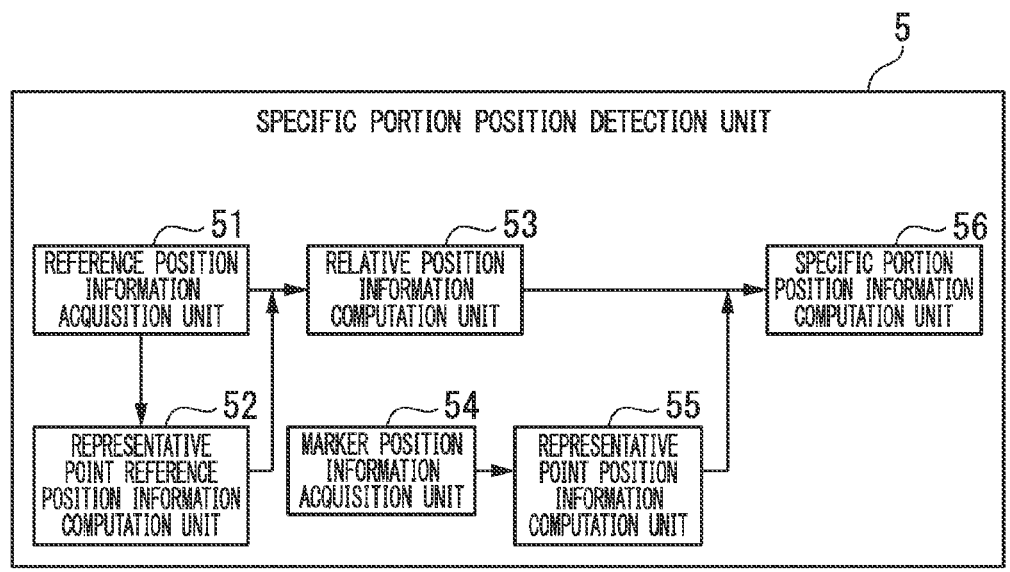
FIG. 4 is a block diagram illustrating a specific portion position detection unit of the present invention.

FIG. 4 is a functional block diagram of the specific portion position detection unit 5.

As illustrated in FIG. 4, the specific portion position detection unit 5 includes a reference position information acquisition unit 51, a representative point reference position information computation unit 52, a relative position information computation unit 53, a marker position information acquisition unit 54, a representative point position information computation unit 55, and a specific portion position information computation unit 56.

The reference position information acquisition unit 51 acquires reference position information representing positions of the specific portion 61 and the plurality of markers 62 within the body of the patient 43 at a reference time. The reference position information acquisition unit 51 acquires the reference position information from a three-dimensional CT image generated based on a transmission image captured by the radiotherapy equipment 3. The reference position information of the specific portion 61 and the plurality of markers 62 are represented as three-dimensional coordinates.

The representative point reference position information computation unit 52 generates representative point reference position information representing a position of a representative point of the plurality of markers 62 within the body of the subject at the reference time.

At this time, the representative point reference position information computation unit 52 specifies a weight coefficient for each of the plurality of markers 62. In addition, the representative point reference position information computation unit 52 computes a reference position of the representative point by multiplying three-dimensional coordinates represented by the reference position information for each of the plurality of markers 62 by the weight coefficient of the corresponding marker 62, and generates the representative point reference position information including the reference position of the representative point. The three-dimensional coordinates represented by the reference position information for each of the plurality of markers 62 are acquired by the reference position information acquisition unit 51. Here, in this embodiment, position information of a weighted center of each position represented by the reference position information of the plurality of markers 62 is the representative point reference position information. The representative point reference position information is generated as three-dimensional coordinates.

That is, assuming that coordinates of n-th marker 62 are $(X_n, Y_n, Z_n)$, the number of markers 62 is N, and weight coefficients of the n-th marker 62 are $W_n$, reference position information $(X_{Ga}, Y_{Ga}, Z_{Ga})$ representing a reference position of a representative point $G_a$ can be computed by the following Equations (1a) to (1c).

$$X_{Ga} = (X_1 W_1 + X_2 W_2 + X_3 W_3 + \ldots + X_n W_n)/N \qquad (1a)$$

$$Y_{Ga} = (Y_1 W_1 + Y_2 W_2 + Y_3 W_3 + \ldots + Y_n W_n)/N \qquad (1b)$$

$$Z_{Ga} = (Z_1 W_1 + Z_2 W_2 + Z_3 W_3 + \ldots + Z_n W_n)/N \qquad (1c)$$

The relative position information computation unit 53 generates relative position information of the position represented by the reference position information of the specific portion 61, using a position represented by the representative point reference position information as a base point. The reference position information of the specific portion 61 is acquired by the reference position information acquisition unit 51 as three-dimensional coordinates, and the representative point reference position information is generated as three-dimensional coordinates by the representative point reference position information computation unit 52. Therefore, the relative position information computation unit 53 generates the relative position information according to a difference between the three-dimensional coordinates of the position represented by the reference position information of the specific portion 61 and the three-dimensional coordinates of the position represented by the representative point reference position.

The marker position information acquisition unit 54 acquires position information of the plurality of markers 62 at time t different from the reference time after the passage of a predetermined time from the reference time. In this process, the marker position information acquisition unit 54 acquires the position information of the plurality of markers 62 at time t from a three-dimensional CT image generated by the radiotherapy equipment 4 in the same way as the reference position information of the plurality of markers 62 described above. The position information of the plurality of markers 62 are represented as three-dimensional coordinates. Alternatively, the three-dimensional coordinates of the position information of the plurality of markers 62 may automatically determine a portion of luminance corresponding to the marker 62 according to image processing from the three-dimensional CT image and specify the coordinates, and may be input as the position information of the plurality of markers 62. Further, using two-dimensional images captured in two directions instead of the three-dimensional CT image, the portion of the luminance corresponding to the marker 62 may be automatically determined according to image processing and the coordinates may be specified and input as the position information of the plurality of markers 62.

The representative point position information computation unit 55 generates representative point position information at time t from the position information of the plurality of markers 62 at time t different from the reference time acquired by the marker position information acquisition unit 54. Here, the representative point position information computation unit 55 specifies a weight coefficient for each of the plurality of markers 62 in the same way as the representative point reference position information computation unit 52 does. In addition, the representative point position information computation unit 55 multiplies the three-dimensional coordinates at time t for each of the plurality of markers 62 by the weight coefficient specified for each of the plurality of markers 62, computes a position of the representative point, and generates representative point position information. The three-dimensional coordinates at time t for each of the plurality of markers 62 are acquired by the marker position information acquisition unit. In this embodiment, the representative point position information computation unit 55 generates a position of a weighted center at time t of the plurality of markers 62 as the representative point position information. The representative point position information is represented as three-dimensional coordinates. A formula for computation of a position of a representative point $G_b$ is similar to the above-described Equation (1a) through (1c).

The specific portion position information computation unit 56 generates position information of the specific portion 61 at time t from the representative point position information generated by the representative point position information computation unit 55 and the relative position information generated by the relative position information computation unit 53. The specific portion position information computation unit 56 generates the position information of the specific portion 61 at time t by adding three-dimensional coordinates of the position represented by the representative position information to three-dimensional coordinates of the relative position represented by the relative position information at time t.

The specific portion position information computation unit 56 transmits the computed position information of the specific portion 61 at time t to the control unit 4. Based on the position information, the control unit 4 drives the therapeutic radiation irradiation device 16 using the swing mechanism 15 and controls a shape of an irradiation field of the therapeutic radiation 23 using the MLC 20 so that the therapeutic radiation 23 is radiated to a position of the position information. The control unit 4 controls the emission of the therapeutic radiation 23 using the therapeutic radiation irradiation device 16 after driving the swing mechanism 15 and the MLC 20. Also, the control unit 4 can change a positional relationship between the patient 43 and the therapeutic radiation irradiation device 16 further using the turning drive device 11, the traveling drive device, or the couch drive device 42 so that the position of the specific portion 61 is irradiated with the therapeutic radiation 23.

Figure 5:
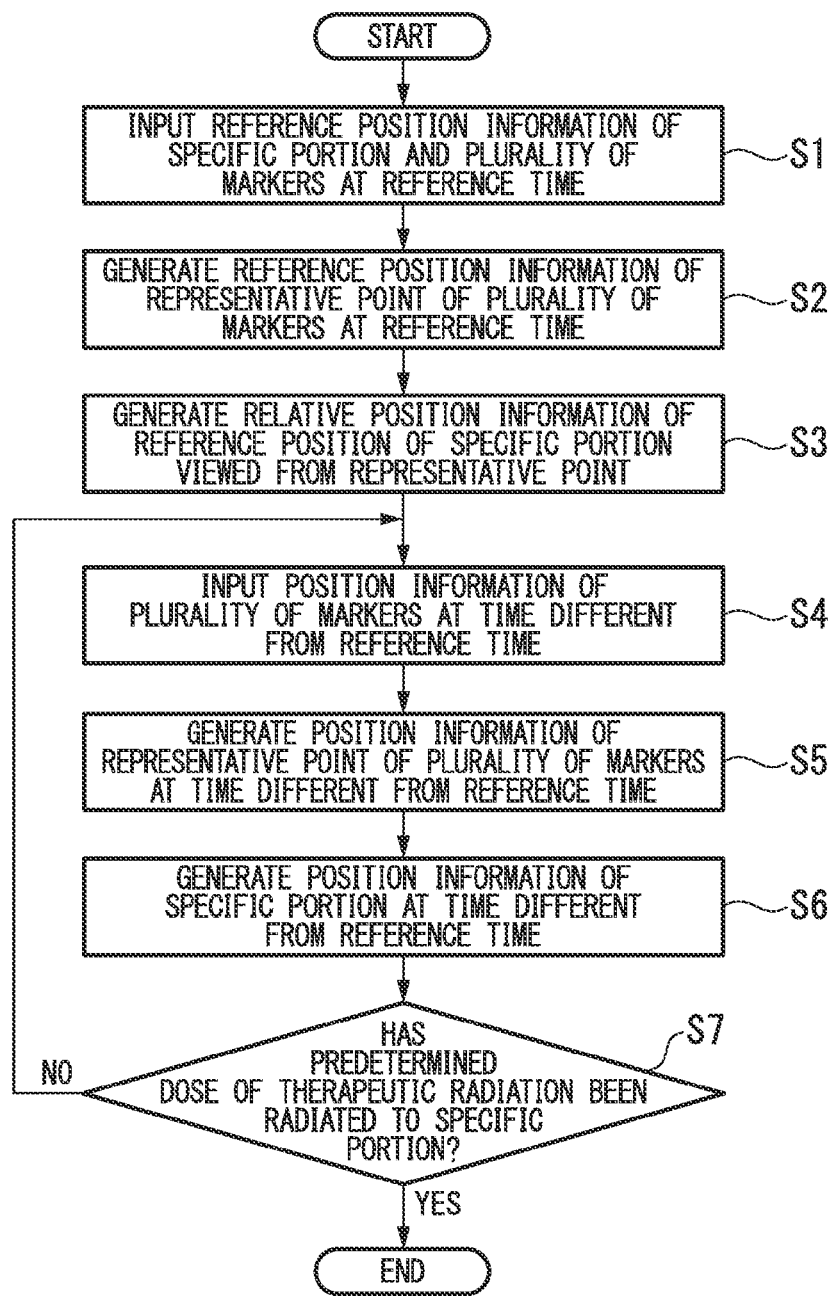
FIG. 5 is a first diagram illustrating a flowchart of a process of the specific portion position detection unit 5.

FIG. 5 is a first diagram illustrating a flowchart of a process of the specific portion position detection unit 5.

A processing flow of the specific portion position detection unit 5 will be described in order next.

First, a user fixes the patient to the couch 41 of the radiotherapy equipment 2, then, generates a transmission image by acquiring images of the specific portion 61 of the patient 43 and the plurality of markers 62 using the imager system of the radiotherapy equipment 4 at a certain reference time. The specific portion position detection unit 5 inputs three-dimensional coordinates as reference position information of the specific portion 61 and the plurality of markers 62 based on a three-dimensional CT image generated from the transmission image (step S1). Here, the three-dimensional coordinates of the reference position information of the plurality of markers 62 may be input based on coordinates designated by a doctor using an input means such as a mouse from the three-dimensional CT image displayed on a screen. In addition, the three-dimensional coordinates of the reference position information of the plurality of markers 62 may be input from a processing unit, after providing the unit to detect intensity from luminance values of the plurality of markers in the CT image and automatically computing the coordinates from the intensity. Likewise, the three-dimensional coordinates of the position information of the specific portion 61 may also be input based on coordinates designated by the doctor using the input means such as the mouse from the three-dimensional CT image displayed on the screen. Alternatively, the three-dimensional coordinates of the position information of the specific portion 61 may automatically be determined by using a pre-stored image of the specific portion 61, automatically determining the specific portion 61 in three-dimensional CT image matched to the pre-stored image by image processing, such as pattern matching, then, a coordinate at the center or the like of a range of the specific portion may be input as the position information of the specific portion 61. may be input a coordinate, like the center of the specific portion, as the position information of the specific portion 61

The specific portion position detection unit 5 generates representative point reference position information of the plurality of markers 62 at the reference time from three-dimensional coordinates representing the reference position information of the plurality of markers 62 acquired in step S1 (step S2). The representative point reference position information is represented as three-dimensional coordinates. A specific generation process will be described later.

Next, the specific portion position detection unit 5 generates relative position information of a position represented by the reference position information of the specific portion 61 using the representative point reference position as the base point (step S3). To be specific, a difference between the three-dimensional coordinates of the position represented by the representative point reference position and the three-dimensional coordinates of the position represented by the reference position information of the specific portion 61 is obtained.

Next, when radiotherapy starts, images of the specific portion 61 of the patient and the plurality of markers 62 are periodically acquired using the imager system of the radiotherapy equipment 3. The specific portion position detection unit 5 inputs the position information of the plurality of markers 62 detected from the three-dimensional CT image generated from the transmission image captured at time t different from the reference time as in step S1 (step S4). Then, the specific portion position detection unit 5 generates representative point position information of the plurality of markers 62 at time t from the position information of the plurality of markers 62 (step S5). The position information of the plurality of markers 62 is represented as three-dimensional coordinates. A specific generation process of the representative point position information of the plurality of markers 62 will be described later.

The specific portion position detection unit 5 generates position information of the specific portion 61 at time t from the relative position information representing the relative position computed in step S3 and the representative point position information representing the position of the representative point at time t computed in step S5 (step S6). To be specific, a position represented by three-dimensional coordinates obtained by adding the three-dimensional coordinates of the position represented by the relative position information to the three-dimensional coordinates of the position represented by the position information of the representative point is generated as the position information of the specific portion 61.

The control unit 4 acquires the position information of the specific portion 61 detected by the specific portion position detection unit 5 in this manner and controls the radiotherapy equipment 3.

In addition, the control unit 4 determines whether the radiotherapy equipment 3 has delivered a predetermined dose of therapeutic radiation 23 to the specific portion 61 (step S7), then, controls repetition of operation from steps S4 to S6 until the predetermined dose is delivered. The dose to be delivered is set in each therapeutic plan.

Figure 6:
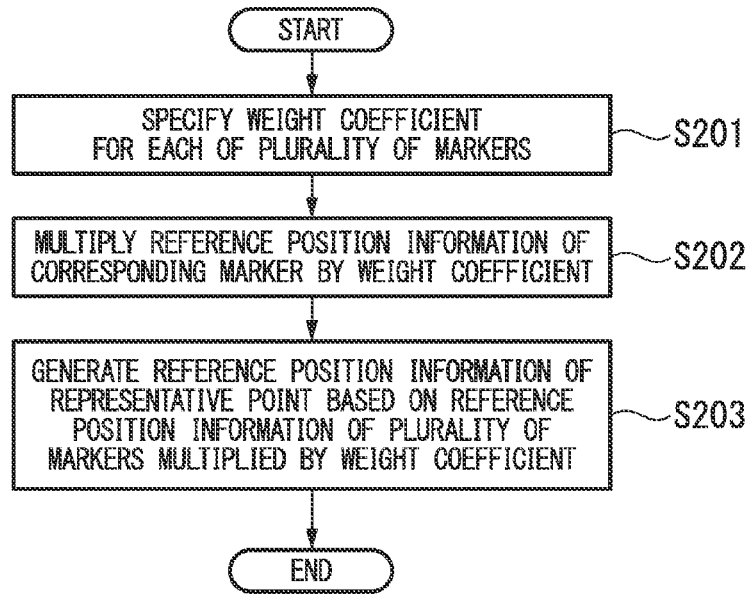
FIG. 6 is a second diagram illustrating the flowchart of the process of the specific portion position detection unit 5.

FIG. 6 is a second diagram illustrating the flowchart of the process of the specific portion position detection unit 5.

Here, the process of computing the reference position information of the plurality of markers 62 in step S2 will be described. The representative point reference position information computation unit 52 of the specific portion position detection unit 5 computes the reference position information of the representative point at the reference time as illustrated in FIG. 6. First, the representative point reference position information computation unit 52 specifies a weight coefficient for each of the plurality of markers 62 (step S201). Like the position information of the marker 62, this weight coefficient is specified in three dimensions. That is, the weight coefficient W is represented in the form of ($W_x$, $W_y$, $W_z$). Next, the representative point reference position information computation unit 52 multiplies three-dimensional coordinates of a position represented by the position information of a corresponding marker 62, by the specified weight coefficient (step S202). The representative point reference position information computation unit 52 generates the position information of the representative point based on the three-dimensional coordinates of the position represented by the position information for each of the plurality of markers 62 by which the computed weight coefficient is multiplied (step S203). A formula for computation is similar to the above-described Equation (1a) through (1c). The representative point reference position information computation unit 52 outputs the position information at the reference time of the representative point of the plurality of markers 62 obtained in this manner, as the representative point reference position information for the plurality of markers 62, to the relative position information computation unit 53.

Now, the above-described weight coefficient will be described more in detail. In this embodiment, the representative point reference position information computation unit 52 computes a reciprocal of a distance between the specific portion 61 and each of the plurality of markers 62 for each of the plurality of markers 62, and specifies the computed reciprocal as the weight coefficient of each of the plurality of markers 62. The representative point reference position information computation unit 52 obtains distances between the specific portion 61 and the plurality of markers 62 according to absolute values of differences between three-dimensional coordinates of a position represented by the reference position information of the specific portion 61 at the reference time and three-dimensional coordinates of positions represented by reference position information of the plurality of markers 62 at the reference time.

Figure 7:
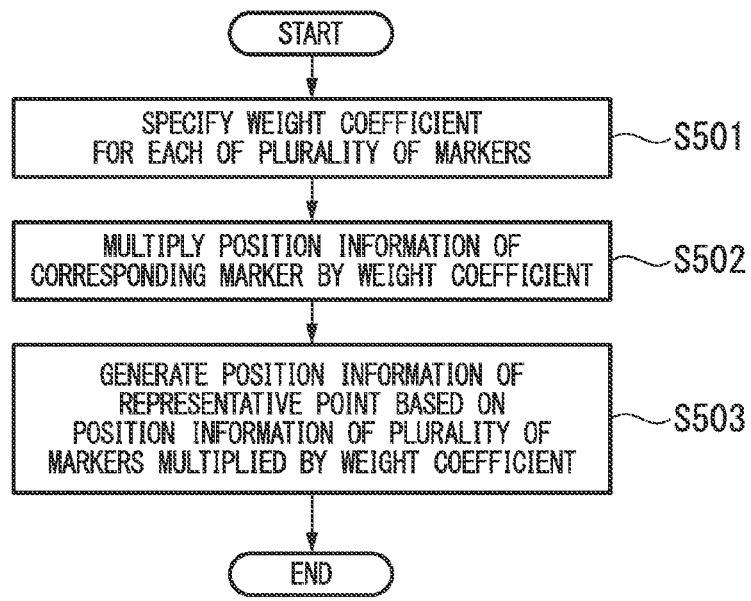
FIG. 7 is a third diagram illustrating the flowchart of the process of the specific portion position detection unit 5.

FIG. 7 is a third diagram illustrating the flowchart of the process of the specific portion position detection unit 5.

Now, the process of computing the position information of the plurality of markers 62 in step S5 will be described.

As illustrated in FIG. 7, the representative point position information computation unit 55 of the specific portion position detection unit 5 generates the position information of the representative point at time t. First, the representative point position information computation unit 55 specifies a weight coefficient for each of the plurality of markers 62 (step S501). Like the position information of the marker 62, the weight coefficient is specified in three dimensions. That is, the weight coefficient W is represented in the form of ($W_x$, $W_y$, $W_z$). Next, the representative point position information computation unit 55 multiplies three-dimensional coordinates of a position represented by the position information of a corresponding marker 62, by the specified weight coefficient (step S502). The representative point position information computation unit 55 generates the position information of the representative point based on the three-dimensional coordinates of the position represented by the position information for each of the plurality of markers 62 by which the computed weight coefficient is multiplied (step S503). A formula for computation is similar to the above-described Equation (1a) through (1c).

In this embodiment, the representative point position information computation unit 55 computes a reciprocal of a distance between the specific portion 61 and each of the plurality of markers 62 for the plurality of markers 62, and specifies the computed reciprocal as the weight coefficient of each of the plurality of markers 62. In addition, the representative point position information computation unit 55 obtains the weight coefficient at time t from the distances between the specific portion 61 and the plurality of markers 62 at the reference time. That is, the representative point position information computation unit 55 obtains the distances between the specific portion 61 and the plurality of markers 62 at the reference time according to absolute values of differences between three-dimensional coordinates of a position represented by the reference position information of the specific portion 61 at the reference time and three-dimensional coordinates of positions represented by reference position information of the plurality of markers 62 at the reference time.

According to this configuration, the radiotherapy equipment control device 2 can obtain the representative point from position information of the plurality of markers 62 by which weight coefficients corresponding to distances from the specific portion 61 are multiplied using the specific portion position detection unit 5. Thus, the weight coefficient of the marker 62 located at a position away from the specific portion 61 decreases, and the weight coefficient of the marker 62 located at a position close to the specific portion 61 increases. The marker 62 located at the position away from the specific portion 61 is considered to have a displacement amount or displacement direction which is different from the specific portion 61 and the marker 62 located at the position close to the specific portion 61 is considered to have a displacement amount or a displacement direction which is similar to the specific portion 61. Therefore, because the representative point can be computed by increasing the weight of the marker 62 having a displacement state which is similar to that of the specific portion 61, the state of the displacement of the representative point can be close to the state of the displacement of the specific portion 61. Thereby, it is possible to improve the accuracy of position detection of the specific portion 61. Thus, by employing the position information of such a specific portion, it will become possible to detect the position of the specific portion with accuracy sufficient for tracking irradiation with the radiotherapy equipment, and it also will be possible to prevent a normal portion other than the specific portion of the patient from being excessively irradiated with therapeutic radiation.

Also, as the weight coefficient to be applied to each of the plurality of markers 62, correlation parameters between displacement amounts from the reference position for the specific portion 61 and displacement amounts from the reference position for the marker 62 at a plurality of different times may be used.

Here, the correlation parameter is a parameter representing a correlation between the displacement amount from the reference position of the specific portion 61 and the displacement amount from the reference position of the marker 62, and it may be computed as a correlation coefficient.

Specifically, the representative point reference position information computation unit 52 or the representative point position information computation unit 55 of the specific portion position detection unit 5 obtains positions represented by position information of the specific portion 61 at a plurality of different times and obtains displacement amounts from the reference position. Likewise, the representative point reference position information computation unit 52 or the representative point position information computation unit 55 of the specific portion position detection unit 5 obtains positions represented by the position information of the marker 62 at a plurality of different times which are the same as when the position of the specific portion 61 is obtained, and obtains displacement amounts from the reference position. The representative point reference position information computation unit 52 or the representative point position information computation unit 55 of the specific portion position detection unit 5 computes a correlation coefficient using the displacement amount from the reference position of the specific portion 61 and the displacement amount from the reference position for each of the markers 62 obtained as described above as two variables. The correlation coefficient represents that the more the correlation coefficient approaches 0, the lower the correlation between the two variables is and represents that the more the correlation coefficient approaches 1, the higher the correlation between the two variables is. The representative point reference position information computation unit 52 or the representative point position information computation unit 55 specifies the computed correlation coefficient as the correlation parameter and uses the specified correlation coefficient as the weight coefficient.

Figures 8, 9:
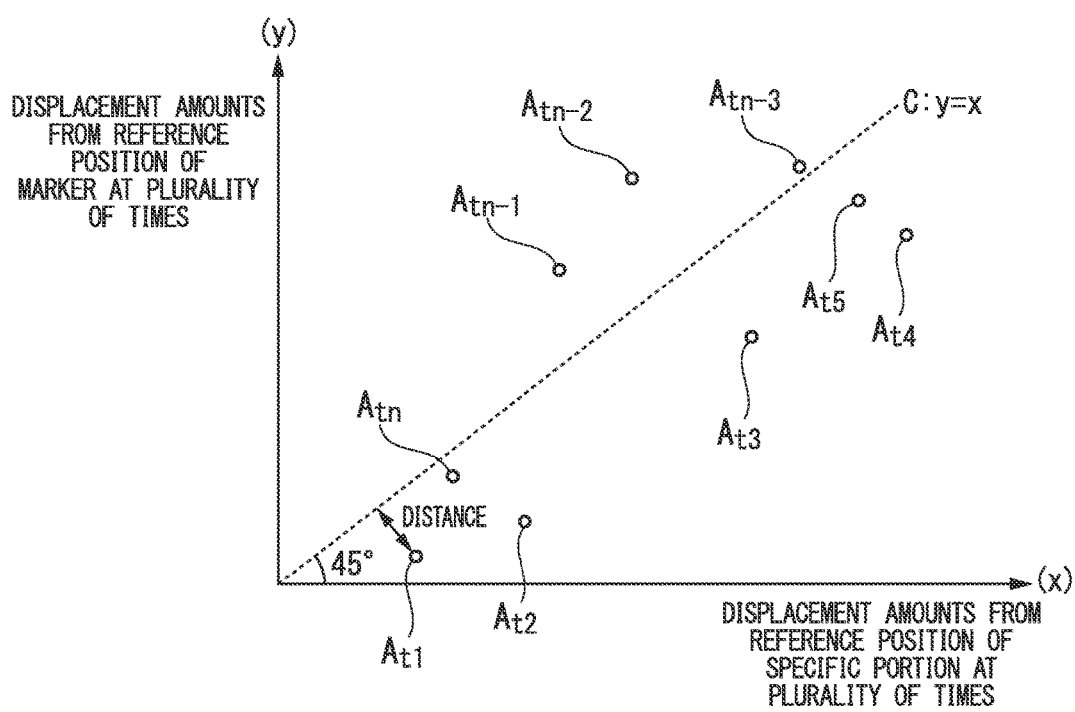
FIG. 8 is a data example illustrating a correspondence relationship between a displacement amount from a reference position of the specific portion and a displacement amount from a reference position of the marker.
FIG. 9 is a diagram illustrating the correspondence relationship between the displacement amount from the reference position of the specific portion and the displacement amount from the reference position of the marker.

In addition, FIG. 8 is a diagram illustrating an example of a computation method of a relative parameter, and is a diagram illustrating relationships between displacement amounts from a reference position of the specific portion at a plurality of times and displacement amounts from a reference position of the marker at the plurality of times. As illustrated in FIG. 8, a correlation parameter may be computed based on the displacement amounts from the reference position of the specific portion 61 at a plurality of different times and used as a weight coefficient.

Specifically, as illustrated in FIG. 8, the representative point reference position information computation unit 52 or the representative point position information computation unit 55 of the specific portion position detection unit 5 computes the displacement amounts from the reference position of the specific portion 61 at the plurality of different times and displacement amounts from the reference position of the marker 62 at the plurality of different times. In FIG. 8, $A_t$ represents a correspondence relationship between a displacement amount from the reference position of the specific portion 61 and a displacement amount from a reference position of one certain marker 62a at time t. For example, $A_{t1}$ represents a correspondence relationship between a displacement amount $x_1$ from the reference position of the specific portion 61 and a displacement amount $y_1$ from the reference position of one certain marker 62a at time $t_1$. Then, the representative point reference position information computation unit 52 or the representative point position information computation unit 55 of the specific portion position detection unit 5 computes a distance between $A_t(x, y)$ and a straight line represented by y=x. Here, the straight line of y=x corresponds to a line connecting a set of $A_t(x, y)$ when the displacement amount x from the reference position of the specific portion 61 and the displacement amount y from a reference position of one certain marker 62a are the same at each of different times t. The representative point reference position information computation unit 52 or the representative point position information computation unit 55 of the specific portion position detection unit 5 computes distances between a plurality of $A_t(x, y)$ and the straight line represented by y=x for the marker 62a, and computes a sum of the distances. Then, a reciprocal of the sum is specified as a correlation parameter and specified as a weight coefficient for the marker 62a. In addition, similar weight coefficient specification is also performed for markers 62 other than the marker 62a.

FIG. 9 is a diagram illustrating the correspondence relationship between the displacement amount from the reference position of the specific portion and the displacement amount from the reference position of the marker.

As illustrated in FIG. 9, a displacement amount from a reference position of the specific portion 61 and a displacement amount from a reference position of one certain marker 62a can be represented by a plot $A_{tn}$ (n=1, 2, . . . , n) as illustrated at each time to (n=1, 2, . . . , n). The representative point reference position information computation unit 52 or the representative point position information computation unit 55 computes a distance between a straight line C having a tilt of 45 degrees formed from a set of plots in which the displacement from the reference position of the specific portion 61 is equal to the displacement from the reference position of the marker 62 and a plot $A_{t1}$, similarly computes a distance of the plot $A_m$ (n=1, 2, ..., n) from the straight line C, and further computes a sum of the distances. It shows that the more the sum of the distances increases, the more displacement amount of the marker 62a is different from the displacement amount of the specific portion 61. In contrast, the more the sum of the distances decreases, the more displacement amount of the marker 62a is similar to the displacement amount of the specific portion 61. The representative point reference position information computation unit 52 or the representative point position information computation unit 55 specifies a reciprocal of the sum as a weight coefficient to be applied to the marker 62a. Likewise, the representative point reference position information computation unit 52 or the representative point position information computation unit 55 specifies weight coefficients for other markers.

According to this configuration, it is possible to obtain a representative point by multiplying a high weight coefficient with respect to a marker 62 representing a high correlation with the specific portion 61. Thus, a displacement state of the representative point can approach a displacement state of the specific portion 61, and the accuracy of position detection of the specific portion 61 can be improved.

In addition, when the displacement state is different even when the marker 62 is located in the vicinity of the specific portion 61, for example, even when the marker 62 is located in the vicinity of a heart of a subject and significantly affected by the pulsation of the heart, etc., it is still possible to accurately detect the position of the specific portion 61.

In addition, the above-described weight coefficient may be specified by an arbitrary input by the user through the input means.

According to this configuration, it is possible to arbitrarily specify weight coefficients of the plurality of markers 62 through the user's determination. Therefore, it is possible to detect the position of the specific portion 61 more simply using a representative point to which a weight is assigned for each of the plurality of markers 62.

In addition, a weight coefficient of at least one marker 62 among the plurality of markers 62 may be specified as 0.

According to this configuration, it is possible to exclude a marker 62 having an obviously different displacement state from the specific portion 61 or a marker 62 determined to be improper for use in position detection of the specific portion 61 for any reasons from subsequent computation for the position detection of the specific portion 61. Thereby, it is possible to detect the position of the specific portion 61 more accurately.

Also, a marker 62 to be used for computation of the position detection of the specific portion 61 can be arbitrarily selected in place of specifying the weight coefficient of at least one marker 62 among the plurality of markers 62 as 0.

Although the exemplary embodiments of the present invention have been described in detail above with reference to the drawings, specific configurations are not limited to the embodiments, and a design change, etc. may also be included without departing from the scope of the present invention.

Each device described above may internally include a computer system. Therefore, the steps of each of the above-described processes are stored in a program format on a computer-readable recording medium, and the above-described processes are executed by computer to read and execute the program. The computer-readable recording medium refers to a magnetic disk, a magneto-optical disc, a compact disc-read only memory (CD-ROM), a digital versatile disc (DVD)-ROM, a semiconductor memory, or the like. The computer program may be configured to be distributed to a computer via a communication circuit and executed by the computer receiving the distribution.

In addition, the above-described program may be used to implement some of the above-described functions.

Further, the above-described program may also be a program capable of implementing the above-described functions in combination with a program already recorded on the computer system, that is, a so-called differential file (differential program).

INDUSTRIAL APPLICABILITY

According to some aspects of the present invention, it is possible to provide a radiotherapy equipment control device capable of accurately estimating a position of an irradiation target using a plurality of markers.

DESCRIPTION OF THE REFERENCE SYMBOLS

2 Radiotherapy equipment control device
51 Reference position information acquisition unit
52 Representative point position information computation unit
53 Relative position information computation unit
54 Marker position information acquisition unit
55 Representative point position information computation unit
56 Specific portion position information computation unit
61 Specific portion (affected part)
62 Marker

The invention claimed is:

1. A radiotherapy equipment control device that specifies a position of a specific portion from positions of a plurality of markers in a subject and controls radiotherapy equipment, the radiotherapy equipment control device comprising:
a reference position information acquisition unit configured to acquire reference position information representing a position within the body of the subject at a reference time of each of the specific portion and the plurality of markers, using an image captured at the reference time by the radiotherapy equipment;
a representative point reference position information computation unit configured to generate reference position information representing a position within the body of the subject at the reference time of a representative point of the plurality of markers from the reference position information of the plurality of markers;
a relative position information computation unit configured to generate relative position information of a position represented by the reference position information of the specific portion using a position represented by the reference position information of the representative point as a base point;
a marker position information acquisition unit configured to acquire position information of the plurality of markers within the body of the subject at another time different from the reference time, using an image captured at the another time by the radio therapy equipment;
a representative point positon information computation unit configured to generate position information of the representative point within the body of the subject at the another time of the plurality of markers from the position information of the plurality of markers; and a specific portion position information computation unit configured to generate position information of the specific portion at the another time from the position information of the representative point and the relative position information, wherein:

the radiotherapy equipment is controlled so as to deliver therapeutic radiation to the specific portion using the position information of the specific portion at the another time;

the markers are embedded in the vicinity of the specific portion within the subject;

the representative point reference position information computation unit specifies a displacement-based or distance-based weight coefficient for each of the plurality of markers and generates the reference position information of the representative point based on the position information of the plurality of markers weighted by the weight coefficient, and the representative point position information computation unit generates the position information of the representative point based on the position information of the plurality of markers weighted by the weight coefficient.

2. The radiotherapy equipment control device according to claim 1, wherein the representative point reference position information computation unit and the representative point position information computation unit compute a reciprocal of a distance between the specific portion and the marker for each of the plurality of markers and specify the computed reciprocal as the weight coefficient for each of the plurality of markers.

3. The radiotherapy equipment control device according to claim 1, wherein the representative point reference position information computation unit and the representative point position information computation unit compute and specify the weight coefficient as a correlation coefficient between displacement amounts from a reference position for the specific portion and displacement amounts from a reference position for the marker at a plurality of different times.

4. The radiotherapy equipment control device according to claim 1, wherein the representative point reference position information computation unit and the representative point position information computation unit specify the weight coefficient by an arbitrary input through an input means based on a correlation between displacements of the specific portion and the marker or a distance between the specific portion and the marker.

5. The radiotherapy equipment control device according to claim 1, wherein the representative point reference position information computation unit and the representative point position information computation unit specify the weight coefficient of at least one marker among the plurality of markers as 0.

6. A radiotherapy equipment control method of controlling radiotherapy equipment in specifying a positon of a specific portion from positions of a plurality of markers in a subject, the radiotherapy equipment control method comprising:

acquiring reference position information representing a position within the body of the subject at a reference time of each of the specific portion and the plurality of markers, using an image captured at the reference time by the radiotherapy equipment;

generating refence position information representing a position within the body of the subject at the reference time of a representative point of the plurality of markers from the reference position information of the plurality of markers;

generating relative position information using a position represented by the reference position information of the representative point as a base point for a position represented by the reference position information of the specific portion;

acquiring position information of the plurality of markers within the body of the subject at another time different from the reference time, using an image captured at the another time by the radio therapy equipment;

generating position information of the representative point within the body of the subject at the another time of the plurality of markers from the position information of the plurality of markers;

generating position information of the specific portion at the another time from the position information of the representative point and the relative position information; and controlling the radiotherapy equipment so as to deliver therapeutic radiation to the specific portion using the position information of the specific portion at the another time wherein:

the markers are embedded in the vicinity of the specific portion within the subject, the reference position information of the representative point specifies a displacement-based or distance-based weight coefficient for each of the plurality of markers and is generated based on the position information of the plurality of markers weighted by the weigh coefficient, and the position information of the representative point is generated based on the position information of the plurality of markers weighted by the weight coefficient.

7. A non-transitory computer-readable storage medium having a program encoded thereon, the program for causing a computer of a radiotherapy equipment control device for controlling radiotherapy equipment in specifying a position of a specific portion from positions of a plurality of markers in a subject to execute:

a reference position information acquisition process acquiring reference position information representing a position within the body of the subject at a reference time of each of the specific portion and the plurality of markers, using an image captured at the reference time by the radiotherapy equipment;

a representative point reference position information computation process generating reference position information representing a position within the body of the subject at the reference time of a representative point of the plurality of markers from the reference position information of the plurality of markers;

a relative position information computation process generating relative position information using a position represented by the reference position information of the representative point as a base point for a position represented by the reference position information of the specific portion;

a marker position information acquisition process acquiring position information of the plurality of markers within the body of the subject at another time different than the reference time, using an image captured at the another time by the radiotherapy equipment;

a representative point position information computation process generating position information of the representative point within the body of the subject at the another time of the plurality of markers from the position information of the plurality of markers; and a specific portion position information computation process generating position information of the specific potion at the another time from the position information of the representative point and the relative position information, wherein the radiotherapy equipment is controlled so as to deliver therapeutic radiation to the specific portion using the position information of the specific portion at the another time, the markers are embedded in the vicinity of the specific portion within the subject, a displacement-based or distance-based weight coefficient for each of the plurality of markers is specified, and the reference position information of the representative point based on the position information of the plurality of markers weighted by the weight coefficient in the representative point reference position information computation process, and the position information of the representative point is generated based on the position information of the plurality of markers weighted by the weight coefficient in the representative point position information computation process.

* * * * *